US012797023B2

(12) United States Patent
Rooney et al.

(10) Patent No.: US 12,797,023 B2
(45) Date of Patent: Nov. 17, 2026

(54) LONG IMAGE MULTI-FIELD OF VIEW PREVIEW

(71) Applicant: Medtronic Navigation, Inc., Louisville, CO (US)

(72) Inventors: Elizabeth Rose Rooney, Waltham, MA (US); Amir Eftekhar, Sudbury, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

(21) Appl. No.: 18/626,141

(22) Filed: Apr. 3, 2024

(65) Prior Publication Data

US 2024/0382169 A1 Nov. 21, 2024

Related U.S. Application Data

(60) Provisional application No. 63/466,642, filed on May 15, 2023.

(51) Int. Cl.

*A61B 6/00* (2024.01)
*A61B 5/00* (2006.01)
*G06T 7/73* (2017.01)

(52) U.S. Cl.

CPC ............ *A61B 6/488* (2013.01); *A61B 5/0037* (2013.01); *G06T 7/73* (2017.01); (Continued)

(58) Field of Classification Search

None
See application file for complete search history.

(56) References Cited

U.S. PATENT DOCUMENTS 6,273,606 B1 * 8/2001 Dewaele .............. A61B 6/5241 378/98.12
2014/0098932 A1 4/2014 Profio et al.
(Continued)

FOREIGN PATENT DOCUMENTS

EP 4159129 4/2023

OTHER PUBLICATIONS

International Search Report and Written Opinion for International (PCT) Patent Application No. PCT/US2024/027919, dated Jul. 15, 2024 14 pages.

*Primary Examiner* — Katherine L Fernandez
(74) *Attorney, Agent, or Firm* — Sheridan Ross PC

(57) ABSTRACT

A system may perform a preview scan process associated with scanning a patient anatomy. Performing the preview scan process may include capturing a first localization image based on a start position associated with the preview scan process, capturing a second localization image based on a stop position associated with the preview scan process, and capturing one or more intermediate localization images based on one or more intermediate positions different from the start position and the stop position. The system may generate a multiple field of view representation of the patient anatomy in response to performing the preview scan process. The system may perform a long scan process associated with scanning the patient based on the first localization image, the second localization image, and the one or more localization images. Performing the long scan process may include capturing multidimensional images comprising the patient anatomy, based on the localization images.

20 Claims, 8 Drawing Sheets

(52) U.S. Cl.
CPC ............... *G06T 2207/10028* (2013.01); *G06T 2207/10081* (2013.01); *G06T 2207/10088* (2013.01); *G06T 2207/10116* (2013.01); *G06T 2207/20221* (2013.01); *G06T 2207/30012* (2013.01)

(56) References Cited

U.S. PATENT DOCUMENTS

| | | | | |
|---|---|---|---|---|
| 2020/0037962 | A1* | 2/2020 | Shanbhag ............ | A61B 5/7267 |
| 2020/0258243 | A1 | 8/2020 | Chang et al. | |
| 2021/0150704 | A1 | 5/2021 | Bruening et al. | |
| 2023/0169753 | A1* | 6/2023 | Helm ..................... | G06V 10/40<br>382/103 |
| 2024/0115226 | A1* | 4/2024 | Li ........................ | A61B 6/0407 |
| 2024/0252127 | A1* | 8/2024 | Gerhardson ........... | A61B 6/488 |

* cited by examiner

LONG IMAGE MULTI-FIELD OF VIEW PREVIEW

CROSS-REFERENCE TO RELATED APPLICATIONS

The present application claims the benefit of and priority to U.S. Provisional Application No. 63/466,642 filed on May 15, 2023, entitled "LONG IMAGE MULTI-FIELD OF VIEW PREVIEW", which application is incorporated herein by reference in its entirety.

FIELD OF INVENTION

The present disclosure is generally directed to imaging, and relates more particularly to surgical imaging.

BACKGROUND

Surgical robots may assist a surgeon or other medical provider in carrying out a surgical procedure, or may complete one or more surgical procedures autonomously. Imaging may be used by a medical provider for diagnostic and/or therapeutic purposes. Patient anatomy can change over time, particularly following placement of a medical implant in the patient anatomy.

BRIEF SUMMARY

Example aspects of the present disclosure include:

A system including: a processor; and a memory storing instructions thereon that, when executed by the processor, cause the processor to: perform a preview scan process associated with scanning a patient anatomy, wherein performing the preview scan process includes: capturing a first localization image based on a start position associated with the preview scan process; capturing a second localization image based on a stop position associated with the preview scan process; and capturing one or more intermediate localization images based on one or more intermediate positions different from the start position and the stop position; and perform a long scan process associated with scanning the patient anatomy based on the first localization image, the second localization image, and the one or more intermediate localization images.

Any of the aspects herein, wherein the instructions are further executable by the processor to: calculate one or more parameters associated with an image acquisition path based on the first localization image, the second localization image, and the one or more intermediate localization images; and perform the long scan process associated with scanning the patient anatomy based on the one or more parameters associated with the image acquisition path.

Any of the aspects herein, wherein the instructions are further executable by the processor to: generate a multiple field of view representation of the patient anatomy in response to performing the preview scan process, wherein generating the multiple field of view representation includes providing synchronized navigation of the first localization image, the second localization image, and the one or more intermediate localization images.

Any of the aspects herein, wherein: the first localization image includes at least a first portion of the patient anatomy; the second localization image includes at least a second portion of the patient anatomy; and the one or more intermediate localization images include at least a third portion of the patient anatomy.

Any of the aspects herein, wherein the one or more intermediate positions are between the start position and the stop position with respect to a first axis.

Any of the aspects herein, wherein the instructions are further executable by the processor to: identify target coordinates corresponding to a target region included in at least one localization image among the first localization image, the second localization image, and the one or more intermediate localization images, wherein performing the long scan process is based on the target coordinates.

Any of the aspects herein, wherein the instructions are further executable by the processor to: calculate one or more parameters associated with an image acquisition path based on the target coordinates; and perform the long scan process associated with scanning the patient anatomy based on the one or more parameters associated with the image acquisition path.

Any of the aspects herein, wherein identifying the target coordinates is in response to a user selection of at least one of: the target region included in the at least one localization image; and a target portion of the patient anatomy, wherein the target portion is included in the target region.

Any of the aspects herein, wherein identifying the target coordinates is in response to detecting a target feature included in the target region, wherein the target feature is associated with the patient anatomy.

Any of the aspects herein, wherein: the target region included in the at least one localization image includes at least a portion of the patient anatomy.

Any of the aspects herein, wherein the instructions executable by the processor to perform the long scan process are further executable by the processor to: capture a set of multidimensional images including the patient anatomy based on the first localization image, the second localization image, and the one or more intermediate localization images; and generate a long scan image including the patient anatomy based on merging data associated with the set of multidimensional images.

Any of the aspects herein, wherein the set of multidimensional images include an X-ray image, a computed tomography (CT) image, or a magnetic resonance imaging (MRI) image.

Any of the aspects herein, wherein the long scan image depicts at least a curved portion of the patient anatomy.

Any of the aspects herein, wherein the patient anatomy includes a spinal structure.

Any of the aspects herein, wherein the patient anatomy includes soft tissue.

Any of the aspects herein, wherein: the first localization image, the second localization image, and the one or more intermediate localization images each include an X-ray image, a computed tomography (CT) image, a magnetic resonance imaging (MRI) image, an optical image, or a light detection and ranging (LiDAR) image.

An imaging device; a processor coupled with the imaging device; and memory coupled with the processor and storing instructions thereon that, when executed by the processor, enable the processor to: perform a preview scan process associated with scanning a patient anatomy, wherein performing the preview scan process includes: capturing a first localization image based on a start position associated with the preview scan process; capturing a second localization image based on a stop position associated with the preview scan process; and capturing one or more intermediate localization images based on one or more intermediate positions different from the start position and the stop position; and perform a long scan process associated with scanning the patient anatomy using the imaging device, wherein performing the long scan process is based on the first localization image, the second localization image, and the one or more intermediate localization images.

Any of the aspects herein, wherein the instructions are further executable by the processor to: generate a multiple field of view representation of the patient anatomy in response to performing the preview scan process, wherein generating the multiple field of view representation includes providing synchronized navigation of the first localization image, the second localization image, and the one or more intermediate localization images.

Any of the aspects herein, wherein the imaging device includes at least one of an O-arm and a C-arm.

A method including: performing a preview scan process associated with scanning a patient anatomy, wherein performing the preview scan process includes: capturing a first localization image based on a start position associated with the preview scan process; capturing a second localization image based on a stop position associated with the preview scan process; and capturing one or more intermediate localization images based on one or more intermediate positions different form the start position and the stop position; and performing a long scan process associated with scanning the patient anatomy based on the first localization image, the second localization image, and the one or more intermediate localization images.

Any of the aspects herein, further including: generating a multiple field of view representation of the patient anatomy in response to performing the preview scan process, wherein generating the multiple field of view representation includes providing synchronized navigation of the first localization image, the second localization image, and the one or more intermediate localization images.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/implementations in combination with any one or more other aspects/features/implementations.

Use of any one or more of the aspects or features as disclosed herein.

It is to be appreciated that any feature described herein can be claimed in combination with any other feature(s) as described herein, regardless of whether the features come from the same described implementation.

The details of one or more aspects of the disclosure are set forth in the accompanying drawings and the description below. Other features, objects, and advantages of the techniques described in this disclosure will be apparent from the description and drawings, and from the claims.

The preceding is a simplified summary of the disclosure to provide an understanding of some aspects of the disclosure. This summary is neither an extensive nor exhaustive overview of the disclosure and its various aspects, implementations, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, implementations, and configurations of the disclosure are possible utilizing, alone or in combination, one or more of the features set forth above or described in detail below.

Numerous additional features and advantages of the present disclosure will become apparent to those skilled in the art upon consideration of the implementation descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, implementations, and configurations of the disclosure, as illustrated by the drawings referenced below.

DETAILED DESCRIPTION

Figure 1A:
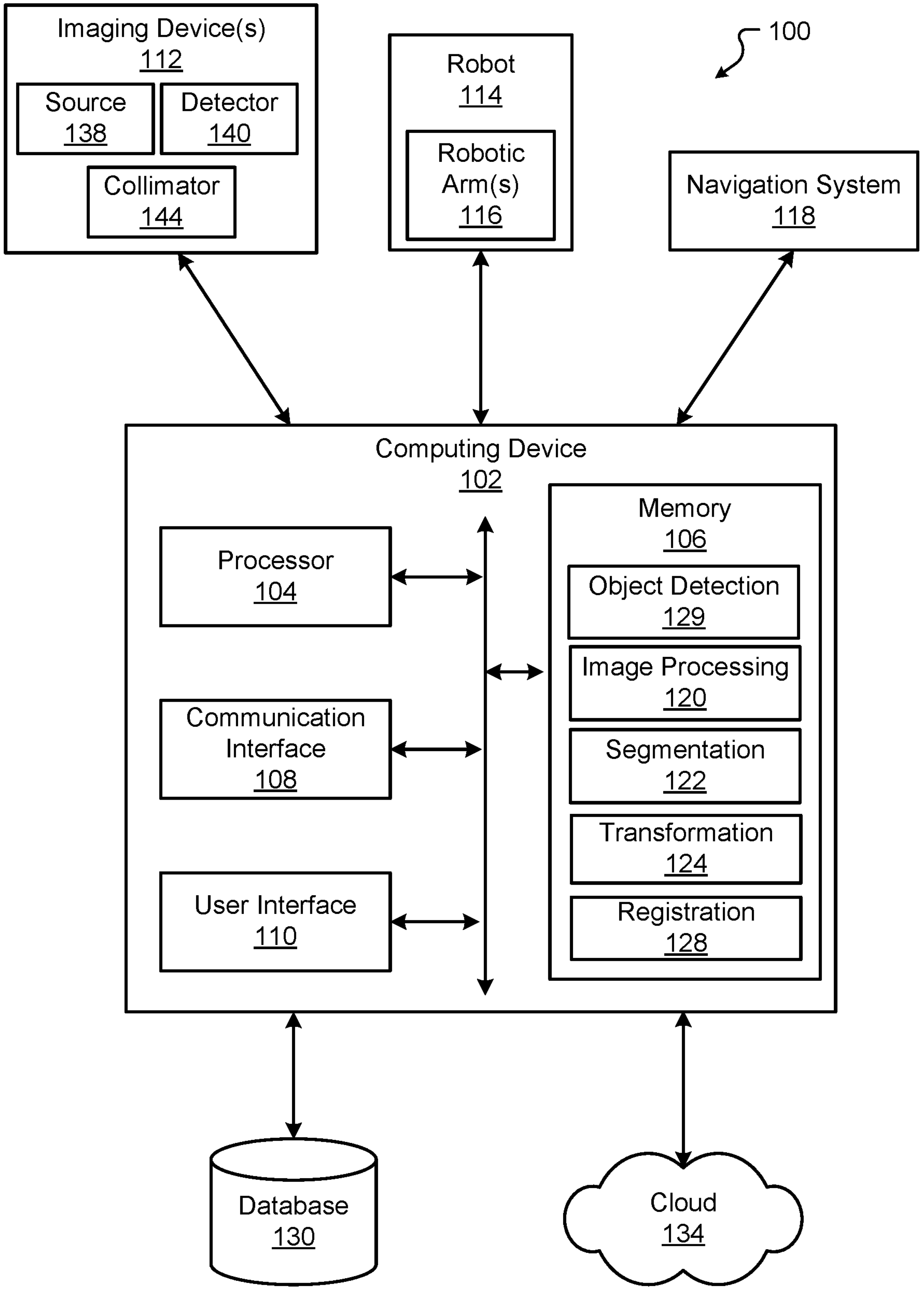
FIGS. 1A through 1C illustrate examples of a system that support aspects of the present disclosure.

It should be understood that various aspects disclosed herein may be combined in different combinations than the combinations specifically presented in the description and accompanying drawings. It should also be understood that, depending on the example or implementation, certain acts or events of any of the processes or methods described herein may be performed in a different sequence, and/or may be added, merged, or left out altogether (e.g., all described acts or events may not be necessary to carry out the disclosed techniques according to different implementations of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia Geforce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any implementations of the disclosure are explained in detail, it is to be understood that the disclosure is not limited in its application to the details of construction and the arrangement of components set forth in the following description or illustrated in the drawings. The disclosure is capable of other implementations and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Some imaging systems may support a long scan process capable of generating a multidimensional "long scan" (also referred to herein as a "long film," "long film image," or "pseudo-panoramic image") of a patient anatomy using an imaging device. For example, performing a long scan may produce a long film based on multiple images captured by an imaging device, which may provide a relatively longer or wider image compared to an individual image captured by the imaging device.

In some 2D long film and 3D long scan workflows using an imaging device (e.g., an O-arm, etc.), a user may set the length associated with the scan by locating and saving a start position and a stop position. However, when performing a long scan of the spine of a patient to analyze spinal deformities, the long scan may fail to image a deformity (e.g., curvature) of the spinal anatomy due to the deformity being absent from regions associated with the start and stop positions. For example, there is a possibility that the deformity in the spine anatomy between the start and stop positions will fail to be captured in the resultant long scan image. In some cases, a consequence associated with missing a section of the spine in the image may include a retaking of the long scan image of the spine, which would result in increased radiation exposure (e.g., radiation dose) to the patient due to the rescan and increased surgery time.

Some imaging systems may support capturing images of a patient anatomy using an imaging device. In some 2D long film and 3D long scan workflows, the workflow includes acquiring capturing 2D "scout images" (also referred to herein as "localization images") prior to a subsequent process for capturing a 2D long film or 3D long scan.

The O-Arm® imaging system provided by Medtronic Navigation, Inc. supports providing a field of view (FOV) preview feature (also referred to herein as a FOV preview representation and a multiple FOV representation). Via the FOV preview representation, a user may view acquired 2D scout images, prior to the imaging system acquiring a 2D long film or 3D long scan based on the 2D scout images. Via the FOV preview representation, the imaging system may display to users how movement of the imaging system correlates to the patient anatomy captured in the 2D scout images.

In accordance with aspects of the present disclosure, the systems and techniques described herein support capturing "scout images" (also referred to herein as "localization images") prior to a subsequent scan. For example, the scout images may provide a user with a survey of a region of interest. The scout images may provide anatomical information based on which the system or a user may localize a target patient anatomy (e.g., target spine structures). In some examples, aspects of the present disclosure support using the localization provided by the scout images in conjunction with multiple imaging types (e.g., X-ray imaging, computed tomography (CT) imaging, magnetic resonance imaging (MRI), optical imaging, light detection and ranging (LiDAR) imaging, camera images from an O-arm, preoperative images, intraoperative images, etc.).

According to some example aspects, in addition to capturing scout images at a start position and a stop position in association with a long scan process, the techniques described herein include capturing an additional scout image at an intermediate position between the start position and stop position. Additionally, or alternatively, the techniques described herein may include capturing multiple additional scout images at respective intermediate positions between the start position and stop position.

Based on the acquired scout images, the systems and techniques described herein may provide a preview feature (also referred to herein as a "multi-field of view preview" feature or "field of view preview" feature) that supports user based adjustments to an imaging device (e.g., position adjustments, orientation adjustments, etc. to an O-arm imaging device) in association with capturing an anatomy of interest. In some examples, the systems and techniques described herein may implement the preview feature in response to a user input. As will be described herein, the systems and techniques may support user based adjustments for ensuring that the entirety of the anatomy of interest will be captured in the final long scan image.

In some aspects, the preview feature may support adjusting acquired scout images and displaying how adjustments of the imaging device (e.g., O-arm imaging device, etc.) will translate to a new area of the image being captured. For example, the preview feature may support adjustments to acquired scout images (e.g., recentering of the scout images, etc.) based on user selected coordinates in one or more of the acquired scout images, and based on the adjustments, the system may provide a preview of which portions of the anatomy will be captured in a long scan image. In an example, once the adjustments to each of the scout images using the preview feature are complete, the system may calculate an image acquisition path based on the adjustments and update locations associated with the start position, intermediate position(s), and stop position.

Accordingly, for example, for cases where a patient has a severely deformed spine, some long scan workflows may acquire scout images at start and stop positions associated with a long scan, which may fail to account for capturing all the curvature associated with the severely deformed spine. The techniques described herein of adding (and in some cases, optionally adding) a scout image between the start and stop positions (e.g., in the middle of the scan) in association with the generation of a long scan image will allow users to ensure that the entirety of the anatomy is captured in the long scan image.

Aspects of the present disclosure may support imaging in association with spine surgery procedures, for example, for deformity cases (e.g., adult deformity, adolescent idiopathic scoliosis, etc.). For example, the imaging techniques described herein may support the generation or capture of extended 2D images of the spine (e.g., for visualizing spine alignment) and extended 3D images of the spine (e.g., for navigated spine procedures). As will be described and illustrated herein, extended 2D images and extended 3D images may include images captured based on 2D long film and 3D long scan workflows using an imaging device (e.g., an O-arm, etc.). Examples of extended 2D images and extended 3D images include long scan images described herein. In some aspects, a long scan image described herein may be acquired based on multiple localization images, and a size of the long scan image may be greater than a corresponding size of each localization image at least with respect to a dimension. In an example, the dimension may correspond to a scan direction associated with acquiring the long scan image.

Implementations of the present disclosure provide technical solutions to one or more of the problems of radiation exposure to operators, surgeons, and patients. X-ray exposure can be quantified by dose, or the amount of energy deposited by radiation in tissue. Ionizing radiation can cause debilitating medical conditions. The long scan imaging techniques described herein reduce the risk of generating a long scan image which fails to capture an entire anatomy of interest, reducing risk of additional radiation exposure due to generating an additional long scan image.

FIGS. 1A through IC illustrate examples of a system 100 that support aspects of the present disclosure.

Referring to FIG. 1A, the system 100 includes a computing device 102, one or more imaging devices 112, a robot 114, a navigation system 118, a database 130, and/or a cloud network 134 (or other network). Systems according to other implementations of the present disclosure may include more or fewer components than the system 100. For example, the system 100 may omit and/or include additional instances of one or more components of the computing device 102, the imaging device(s) 112, the robot 114, navigation system 118, the database 130, and/or the cloud network 134. In an example, the system 100 may omit any instance of the computing device 102, the imaging device(s) 112, the robot 114, navigation system 118, the database 130, and/or the cloud network 134. The system 100 may support the implementation of one or more other aspects of one or more of the methods disclosed herein.

The computing device 102 includes a processor 104, a memory 106, a communication interface 108, and a user interface 110. Computing devices according to other implementations of the present disclosure may include more or fewer components than the computing device 102. The computing device 102 may be, for example, a control device including electronic circuitry associated with controlling any of the imaging device 112, the robot 114, and the navigation system 118.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging devices 112, the robot 114, the navigation system 118, the database 130, and/or the cloud network 134.

The memory 106 may be or include RAM, DRAM, SDRAM, other solid-state memory, any memory described herein, or any other tangible, non-transitory memory for storing computer-readable data and/or instructions. The memory 106 may store information or data associated with completing, for example, any step of the process flows 300 and 400 described herein, or of any other methods. The memory 106 may store, for example, instructions and/or machine learning models that support one or more functions of the imaging devices 112, the robot 114, and the navigation system 118. For instance, the memory 106 may store content (e.g., instructions and/or machine learning models) that, when executed by the processor 104, enable image processing 120, segmentation 122, transformation 124, registration 128, and/or object detection 129. Such content, if provided as in instruction, may, in some implementations, be organized into one or more applications, modules, packages, layers, or engines.

Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging devices 112, the robot 114, the navigation system 118, the database 130, and/or the cloud network 134.

The computing device 102 may also include a communication interface 108. The communication interface 108 may be used for receiving data or other information from an external source (e.g., the imaging devices 112, the robot 114, the navigation system 118, the database 130, the cloud network 134, and/or any other system or component separate from the system 100), and/or for transmitting instructions, data (e.g., image data, etc.), or other information to an external system or device (e.g., another computing device 102, the imaging devices 112, the robot 114, the navigation system 118, the database 130, the cloud network 134, and/or any other system or component not part of the system 100). The communication interface 108 may include one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, Zig- Bee, and so forth). In some implementations, the communication interface 108 may support communication between the device 102 and one or more other processors 104 or computing devices 102, whether to reduce the time needed to accomplish a computing-intensive task or for any other reason.

The computing device 102 may also include one or more user interfaces 110. The user interface 110 may be or include a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some implementations, the user interface 110 may support user modification (e.g., by a surgeon, medical personnel, etc.) of instructions to be executed by the processor 104 according to one or more implementations of the present disclosure, and/or to user modification or adjustment of a setting of other information displayed on the user interface 110 or corresponding thereto.

In some implementations, the computing device 102 may utilize a user interface 110 that is housed separately from one or more remaining components of the computing device 102. In some implementations, the user interface 110 may be located proximate one or more other components of the computing device 102, while in other implementations, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may include data corresponding to an anatomical feature of a patient, or to a portion thereof. The image data may be or include a preoperative image, an intraoperative image, a postoperative image, or an image taken independently of any surgical procedure. In some implementations, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or include, for example, an ultrasound scanner (which may include, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may include, for example, a transmitter, a receiver, a processor, and one or more antennae), or any other imaging device 112 suitable for obtaining images of an anatomical feature of a patient 148. The imaging device 112 may be contained entirely within a single housing, or may include a transmitter/emitter and a receiver/detector that are in separate housings or are otherwise physically separated.

In some implementations, the imaging device 112 may include more than one imaging device 112. For example, a first imaging device may provide first image data and/or a first image, and a second imaging device may provide second image data and/or a second image. In still other implementations, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The imaging device 112 may include a source 138, a detector 140, and a collimator 144, example aspects of which are later described with reference to FIGS. 1B and 1C.

The robot 114 may be any surgical robot or surgical robotic system. The robot 114 may be or include, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some implementations, the robot 114 may be configured to hold and/or manipulate an anatomical element during or in connection with a surgical procedure. The robot 114 may include one or more robotic arms 116. In some implementations, the robotic arm 116 may include a first robotic arm and a second robotic arm, though the robot 114 may include more than two robotic arms. In some implementations, one or more of the robotic arms 116 may be used to hold and/or maneuver the imaging device 112. In implementations where the imaging device 112 includes two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may include one or more sensors that enable the processor 104 (or a processor of the robot 114) to determine a precise pose in space of the robotic arm (as well as any object or element held by or secured to the robotic arm).

In some implementations, reference markers (e.g., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some implementations, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some implementations, the navigation system 118 may include one or more electromagnetic sensors. In various implementations, the navigation system 118 may be used to track a position and orientation (e.g., a pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some implementations, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The processor 104 may utilize data stored in memory 106 as a neural network. The neural network may include a machine learning architecture. In some aspects, the neural network may be or include one or more classifiers. In some other aspects, the neural network may be or include any machine learning network such as, for example, a deep learning network, a convolutional neural network, a reconstructive neural network, a generative adversarial neural network, or any other neural network capable of accomplishing functions of the computing device 102 described herein. Some elements stored in memory 106 may be described as or referred to as instructions or instruction sets, and some functions of the computing device 102 may be implemented using machine learning techniques.

For example, the processor 104 may support machine learning model(s) which may be trained and/or updated based on data (e.g., training data) provided or accessed by any of the computing device 102, the imaging device 112, the robot 114, the navigation system 118, the database 130, and/or the cloud network 134. The machine learning model (s) may be built and updated by the system 100 based on the training data (also referred to herein as training data and feedback).

In some examples, based on the data, the neural network may generate one or more algorithms (e.g., processing algorithms) supportive of object detection 129.

The database 130 may store information that correlates one coordinate system to another (e.g., imaging coordinate systems, robotic coordinate systems, a patient coordinate system, a navigation coordinate system, etc.). The database 130 may additionally or alternatively store, for example, one or more surgical plans (including, for example, pose information about a target and/or image information about a patient's anatomy at and/or proximate the surgical site, for use by the imaging device 112, robot 114, the navigation system 118, and/or a user of the computing device 102 or of the system 100); one or more images useful in connection with a surgery to be completed or analyzed; and/or any other useful information. The database 130 may additionally or alternatively store, for example, images captured or generated based on image data provided by the imaging device 112.

The database 130 may be configured to provide any such information to the computing device 102 or to any other device of the system 100 or external to the system 100, whether directly or via the cloud network 134. In some implementations, the database 130 may be or include part of a hospital image storage system, such as a picture archiving and communication system (PACS), a health information system (HIS), and/or another system for collecting, storing, managing, and/or transmitting electronic medical records including image data.

In some aspects, the computing device 102 may communicate with a server(s) and/or a database (e.g., database 130) directly or indirectly over a communications network (e.g., the cloud network 134). The communications network may include any type of known communication medium or collection of communication media and may use any type of protocols to transport data between endpoints. The communications network may include wired communications technologies, wireless communications technologies, or any combination thereof.

Wired communications technologies may include, for example, Ethernet-based wired local area network (LAN) connections using physical transmission mediums (e.g., coaxial cable, copper cable/wire, fiber-optic cable, etc.). Wireless communications technologies may include, for example, cellular or cellular data connections and protocols (e.g., digital cellular, personal communications service (PCS), cellular digital packet data (CDPD), general packet radio service (GPRS), enhanced data rates for global system for mobile communications (GSM) evolution (EDGE), code division multiple access (CDMA), single-carrier radio transmission technology (1×RTT), evolution-data optimized (EVDO), high speed packet access (HSPA), universal mobile telecommunications service (UMTS), 3G, long term evolution (LTE), 4G, and/or 5G, etc.), Bluetooth®, Bluetooth® low energy, Wi-Fi, radio, satellite, infrared connections, and/or ZigBee® communication protocols.

The Internet is an example of the communications network that constitutes an Internet Protocol (IP) network consisting of multiple computers, computing networks, and other communication devices located in multiple locations, and components in the communications network (e.g., computers, computing networks, communication devices) may be connected through one or more telephone systems and other means. Other examples of the communications network may include, without limitation, a standard Plain Old Telephone System (POTS), an Integrated Services Digital Network (ISDN), the Public Switched Telephone Network (PSTN), a Local Area Network (LAN), a Wide Area Network (WAN), a wireless LAN (WLAN), a Session Initiation Protocol (SIP) network, a Voice over Internet Protocol (VOIP) network, a cellular network, and any other type of packet-switched or circuit-switched network known in the art. In some cases, the communications network may include of any combination of networks or network types. In some aspects, the communications network may include any combination of communication mediums such as coaxial cable, copper cable/wire, fiber-optic cable, or antennas for communicating data (e.g., transmitting/receiving data).

The computing device 102 may be connected to the cloud network 134 via the communication interface 108, using a wired connection, a wireless connection, or both. In some implementations, the computing device 102 may communicate with the database 130 and/or an external device (e.g., a computing device) via the cloud network 134.

The system 100 or similar systems may be used, for example, to carry out one or more aspects of any of the methods 300 and/or 400 described herein. The system 100 or similar systems may also be used for other purposes.

Figure 1B:
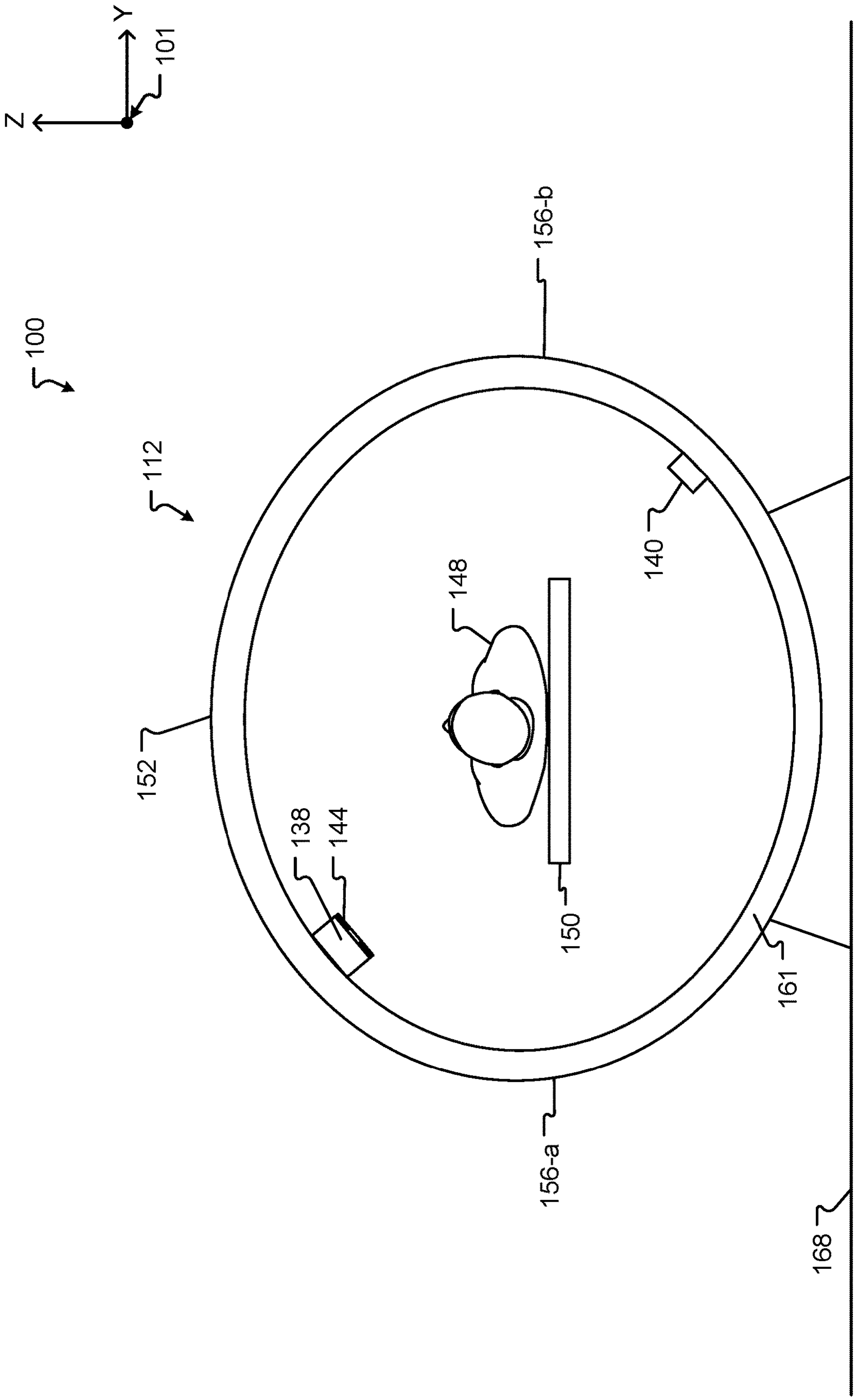

FIG. 1B illustrates an example of the system 100 that supports aspects of the present disclosure. FIG. 1C illustrates an example of the system 100 that supports aspects of the present disclosure. Aspects of the system 100 previously described with reference to FIG. 1A and descriptions of like elements are omitted for brevity.

Figure 1C:
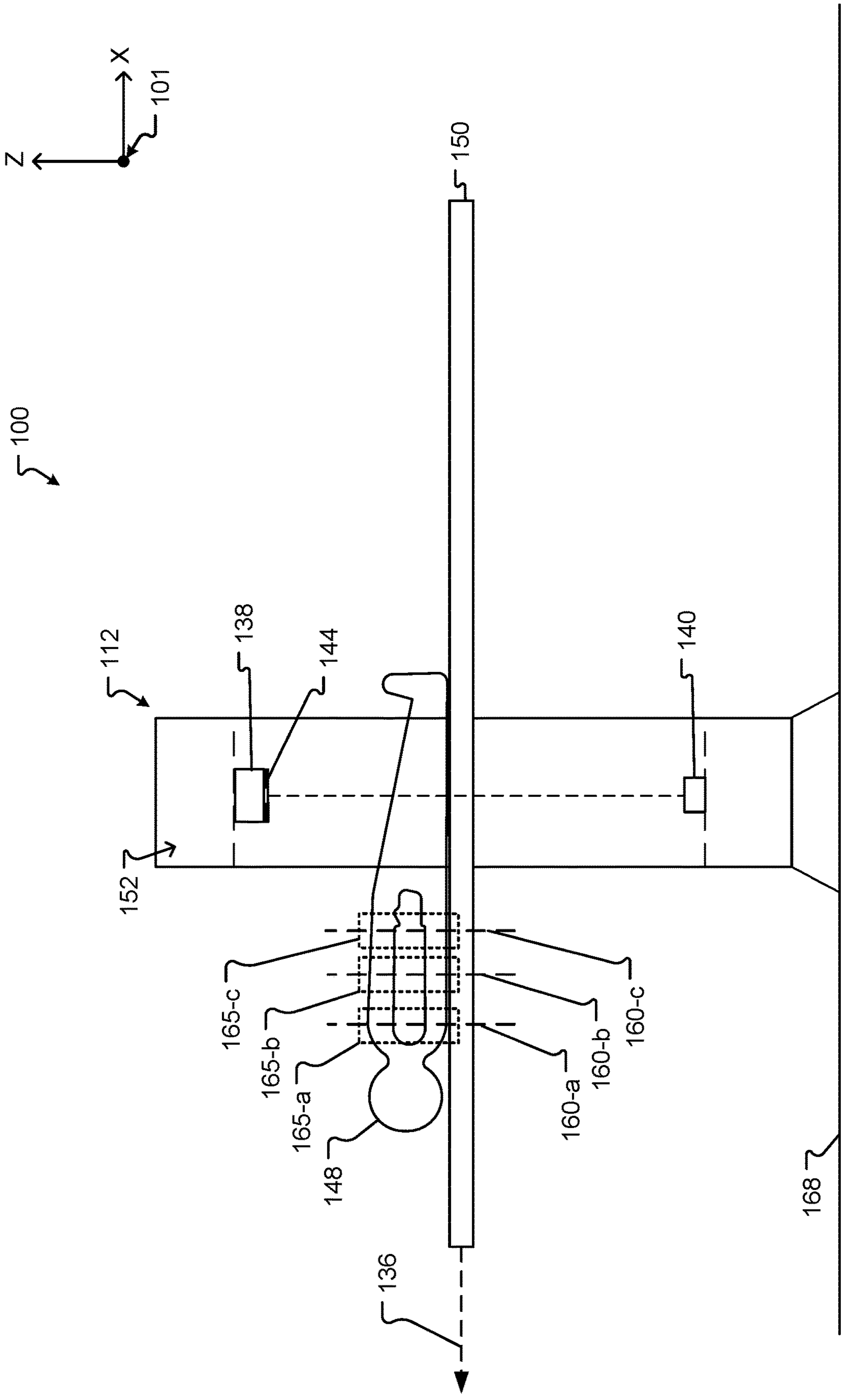

With reference to FIGS. 1B and 1C, features of the system 100 may be described in conjunction with a coordinate system 101. The coordinate system 101, as shown in FIGS. 1B, 1C, and 2A through 2D, includes three-dimensions including an X-axis, a Y-axis, and a Z-axis. Additionally or alternatively, the coordinate system 101 may be used to define planes (e.g., the XY-plane, the XZ-plane, and the YZ-plane) of the system 100. These planes may be disposed orthogonal, or at 90 degrees, to one another. While the origin of the coordinate system 101 may be placed at any point on or near the components of the system 100 (e.g., components of the imaging device 112, for the purposes of description, the axes of the coordinate system 101 are always disposed along the same directions from figure to figure, whether the coordinate system 101 is shown or not. In some examples, reference may be made to dimensions, angles, directions, relative positions, and/or movements associated with one or more components of the system 100 (e.g., imaging device 112) with respect to the coordinate system 101.

The system 100 may be used to initiate long scans of a patient, adjust imaging components to capture localization images of the patient, set or identify target coordinates associated with the localization images, perform a long scan process based on the localization images and the target coordinates, capture multidimensional images based on the target coordinates, and generate a long scan image based on the multidimensional images.

The imaging device 112 includes an upper wall or member 152, a lower wall 161 (also referred to herein as member 161), and a pair of sidewalls 156-*a* and 156-*b* (also referred to herein as members 156-*a* and 156-*b*). In some embodiments, the imaging device 112 is fixed securable to an operating room surface 168 (such as, for example, a ground surface of an operating room or other room). In other embodiments, the imaging device 112 may be releasably securable to the operating room wall 168 or may be a standalone component that is simply supported by the operating room wall 168.

A table 150 configured to support the patient 148 may be positioned orthogonally to the imaging device 112, such that the table 150 extends in a first direction from the imaging device 112. In some embodiments, the table 150 may be mounted to the imaging device 112. In other embodiments, the table 150 may be releasably mounted to the imaging device 112. In still other embodiments, the table 150 may not be attached to the imaging device 112. In such embodiments, the table 150 may be supported and/or mounted to an operating room wall, for example. In embodiments where the table 150 is mounted to the imaging device 112 (whether detachably mounted or permanently mounted), the table 150 may be mounted to the imaging device 112 such that a pose of the table 150 relative to the imaging device 112 is selectively adjustable. The patient 148 may be positioned on the table 150 in a supine position, a prone position, a recumbent position, and the like.

The table 150 may be any operating table configured to support the patient 148 during a surgical procedure. The table 150 may include any accessories mounted to or otherwise coupled to the table 150 such as, for example, a bed rail, a bed rail adaptor, an arm rest, an extender, or the like. The table 150 may be stationary or may be operable to maneuver the patient 148 (e.g., the table 150 may be moveable). In some embodiments, the table 150 has two positioning degrees of freedom and one rotational degree of freedom, which allows positioning of the specific anatomy of the patient anywhere in space (within a volume defined by the limits of movement of the table 150). For example, the table 150 may slide forward and backward and from side to side, tilt (e.g., around an axis positioned between the head and foot of the table 150 and extending from one side of the table 150 to the other) and/or roll (e.g., around an axis positioned between the two sides of the table 150 and extending from the head of the table 150 to the foot thereof). In other embodiments, the table 150 may be bendable at one or more areas (which bending may be possible due to, for example, the use of a flexible surface for the table 150, or by physically separating one portion of the table 150 from another portion of the table 150 and moving the two portions independently). In at least some embodiments, the table 150 may be manually moved or manipulated by, for example, a surgeon or other user, or the table 150 may include one or more motors, actuators, and/or other mechanisms configured to enable movement and/or manipulation of the table 150 by a processor such as a processor 104 of the computing device 102.

The imaging device 112 includes a gantry. The gantry may be or include a substantially circular, or "O-shaped," housing that enables imaging of objects placed into an isocenter thereof. In other words, the gantry may be positioned around the object being imaged. In some embodiments, the gantry may be disposed at least partially within the member 152, the sidewall 156-*a*, the sidewall 156-*b*, and the lower wall 161 of the imaging device 112.

The imaging device 112 also includes a source 138 and a detector 140. The source 138 may be a device configured to generate and emit radiation, and the detector 140 may be a device configured to detect the emitted radiation. In some embodiments, the source 138 and the detector 140 may be or include an imaging source and an imaging detector (e.g., the source 138 and the detector 140 are used to generate data useful for producing images). The source 138 may be positioned in a first position and the detector 140 may be positioned in a second position opposite the source 138. In some embodiments, the source 138 may include an X-ray source (e.g., a thermionic emission tube, a cold emission x-ray tube, or the like). The source 138 may project a radiation beam that passes through the patient 148 and onto the detector 140 located on the opposite side of the imaging device 112. The detector 140 may be or include one or more sensors that receive the radiation beam (e.g., once the radiation beam has passed through the patient 148) and transmit information related to the radiation beam to one or more other components (e.g., processor 104) of the system 100 for processing.

In some embodiments, the detector 140 may include an array. For example, the detector 140 may include three 2D flat panel solid-state detectors arranged side-by-side, and angled to approximate the curvature of the imaging device 112. It will be understood, however, that various detectors and detector arrays can be used with the imaging device 112, including any detector configurations used in typical diagnostic fan-beam or cone-beam CT scanners. For example, the detector 140 may include a 2D thin-film transistor X-ray detector using scintillator amorphous-silicon technology.

The source 138 may be or include a radiation tube (e.g., an x-ray tube) capable of generating the radiation beam. In some embodiments, the source 138 and/or the detector 140 may include a collimator 144 configured to confine or shape the radiation beam emitted from the source 138 and received at the detector 140. Once the radiation beam passes through patient tissue and received at the detector 140, the signals output from the detector 140 may be processed by the processor 104 to generate a reconstructed image of the patient tissue. In this way, the imaging device 112 can effectively generate reconstructed images of the patient tissue imaged by the source 138 and the detector 140.

The source 138 and the detector 140 may be attached to the gantry and configured to rotate 360 degrees around the patient 148 in a continuous or step-wise manner so that the radiation beam can be projected through the patient 148 at various angles. In other words, the source 138 and the detector 140 may rotate, spin, or otherwise revolve about an axis that passes through the top and bottom of the patient 148, with the patient anatomy that is the subject of the imaging positioned at the isocenter of the imaging device 112. The rotation may occur through a drive mechanism that causes the gantry to move such that the source 138 and the detector 140 encircle the patient 148 on the table 150.

At each projection angle, the radiation beam passes through and is attenuated by the patient 148. The attenuated radiation is then detected by the detector 140. The detected radiation from each of the projection angles can then be processed, using various reconstruction techniques, to produce a 2D or 3D reconstruction image of the patient 148. For example, the processor 104 may be used to perform image processing 120 to generate the reconstruction image. Additionally or alternatively, the source 138 and the detector 140 may move along a length of the patient 148, as depicted in FIG. 1B. For example, the table 150 holding the patient 148 may move in the direction of arrow 136 while the source 138 and detector 140 remain in a fixed location, such that the length of the patient can be scanned. In such embodiments, the scanned data may be used to generate one or more reconstructed images of the patient 148 and/or a long scan image of the patient 148.

The imaging device 112 may be included in the O-Arm® imaging system sold by Medtronic Navigation, Inc. having a place of business in Louisville, Colo., USA. The imaging device 112, including the O-Arm® imaging system, or other appropriate imaging systems supportive of aspects of the present disclosure can be found in U.S. Pat. Nos. 7,188,998, 7,108,421, 7,106,825, 7,001,045 and 6,940,941, each of which is incorporated herein by reference. The O-Arm® imaging system can include a mobile cart (not illustrated) that supports movement of the imaging device 112 from one operating theater or room to another, and the gantry may move relative to the mobile cart.

In some example implementations, the system 100 may perform a long scan process by moving the source 138 and the detector 140 along a direction of an axis running through the patient 148. In some embodiments, the direction of the axis along which the source 138 and the detector 140 move may be the same direction as (e.g., extend in a direction parallel to) the direction indicated by the arrow 136. In some embodiments, the long scan process may include moving the patient 148 relative to the source 138 and the detector 140. For example, the patient 148 may be positioned in a prone position on the table 150. The system 100 may move the table 150 through an isocenter of the imaging device 112, in the direction (or opposite the direction) indicated by the arrow 136, such that the source 138 and the detector 140 generate projection data along a length of the patient 148.

In some embodiments, the system 100 may move the source 138 and the detector 140 relative to the patient 148 (or move the table 150 and patient 148 relative to the source 138 and the detector 140) at a predetermined rate and/or a fixed rate. The system 100 may support scanning a patient anatomy (not illustrated) of the patient 148. Examples of the patient anatomy are illustrated at FIGS. 2A through 2F (e.g., patient anatomy 210).

Figure 2B:
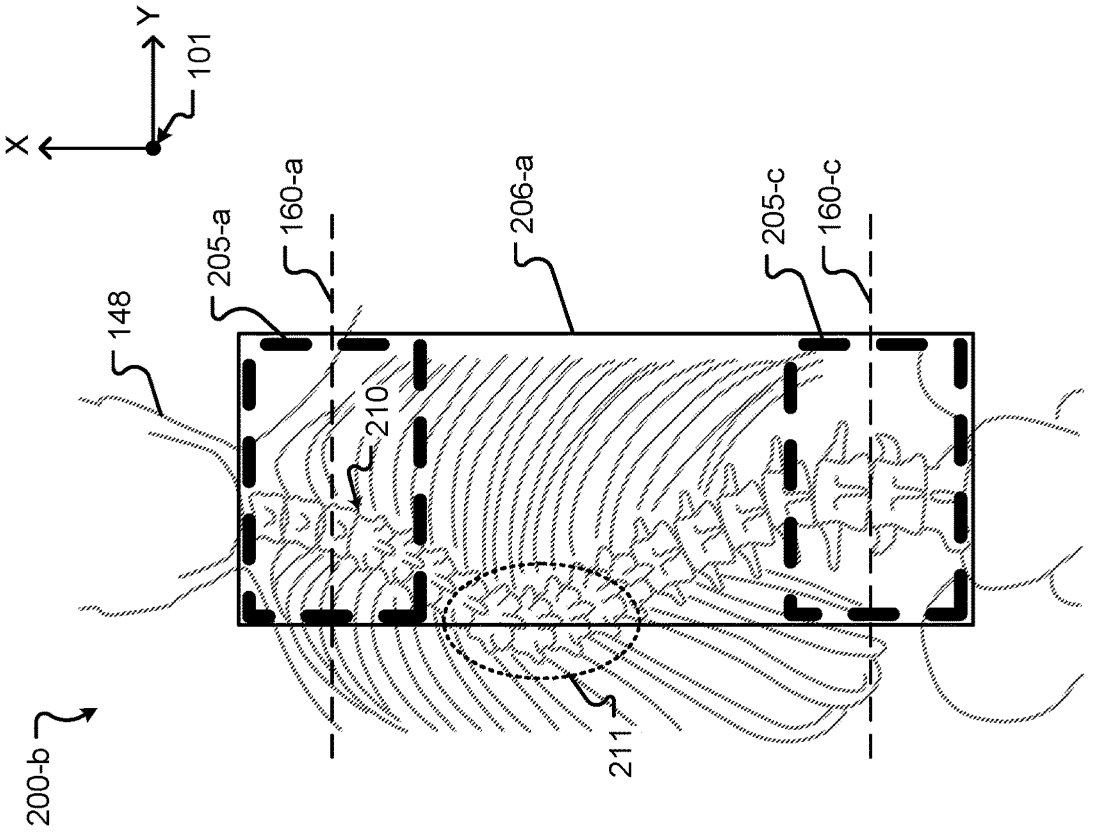
FIG. 2A through 2F illustrates examples of localization images and long scan images supported by aspects of the present disclosure.
Figure 2A:
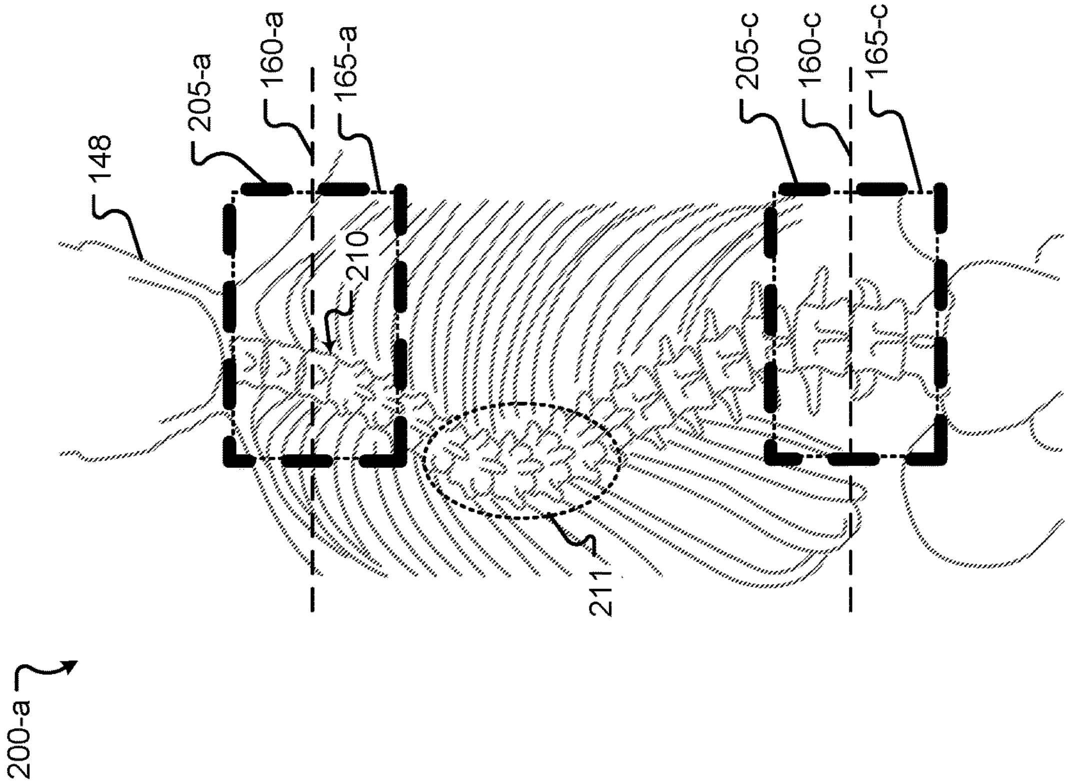

FIG. 2A illustrates an example 200-*a* of localization images 205 supported by aspects of the present disclosure. FIG. 2B illustrates an example 200-*b* of a long scan image 206-*a* supported by aspects of the present disclosure. Aspects of FIG. 2A and FIG. 2B are described with reference to FIG. 1C.

In accordance with aspects of the present disclosure, the system 100 may support the acquisition of localization images 205 (also referred to herein as "scout images" described herein). The localization images 205 may provide anatomical information based on which the system 100 or a user may localize a target patient anatomy (e.g., patient anatomy 210).

In some patient scanning workflows, when implementing a long scan process for generating a multidimensional "long scan" (also referred to herein as a "long film," "long film image," or "pseudo-panoramic image") of a patient anatomy 210 using an imaging device 112, the length of the scan may be configured by setting a start position (e.g., position 160-*a* associated with capturing a region 165-*a*) and a stop position (e.g., position 160-*c* associated with capturing a region 165-*c*) associated with the long scan process. In the example, position 160-*a* may be the center of region 165-*a*, and position 160-*c* may be the center of region 165-*c*. Region 165-*a* and region 165-*c* illustrate examples of what is captured in the localization image 205-*a* and the localization image 205-*c*.

In an example, the patient anatomy 210 may be the spine of a patient 148, and when performing the long scan of the patient anatomy 210 (e.g., spine) to analyze spinal deformities, the long scan may fail to image a deformity (e.g., curvature 211) due to the deformity being absent from the regions 165-*a* and 165-*c* associated with the start and stop positions. For example, in some cases, as illustrated at FIG. 2B, a portion of the deformity (e.g., curvature 211) between the start and stop positions may fail to be captured in the resultant long scan image 206-*a*. In some cases, a consequence associated with missing the deformity (e.g., curvature 211) in the image may include a retaking of an additional long scan image, which would result in increased radiation exposure (e.g., radiation dose) to the patient 148 due to the rescan. Another example consequence associated with missing the deformity is increased surgery time due to time associated with retaking the long scan image.

With reference to FIGS. 2C through 2F, aspects of the present disclosure support capturing one or more additional localization images 205 (e.g., localization image 205-*b*, also referred to herein as an intermediate localization image) between the start and stop positions. The systems and techniques described herein may provide a preview feature (also referred to herein as a “multi-field of view preview” feature or “field of view preview” feature) which displays localization image 205-*a* through localization image 205-*c*. The systems and techniques support user selection of target coordinates (represented by a ‘+’ at FIGS. 2C and 2F). The system 100 may capture multidimensional images based on the target coordinates, and according to example aspects described herein, generate a long scan image 206-*b* from the multidimensional images.

As will be described with reference to FIG. 1C, FIGS. 2C through 2F, and FIG. 3, the systems and techniques described herein support a preview associated with capturing a long scan image 206-*b*, which will allow users to ensure that the entirety of the patient anatomy 210 will be captured in the long scan image 206-*b*. Accordingly, for example, the systems and techniques described herein may prevent additional radiation exposure to the patient 148 (and operators) due to additional long scans, reduce time associated with imaging procedures, reduce time associated with medical procedures, and the like.

Figure 3:
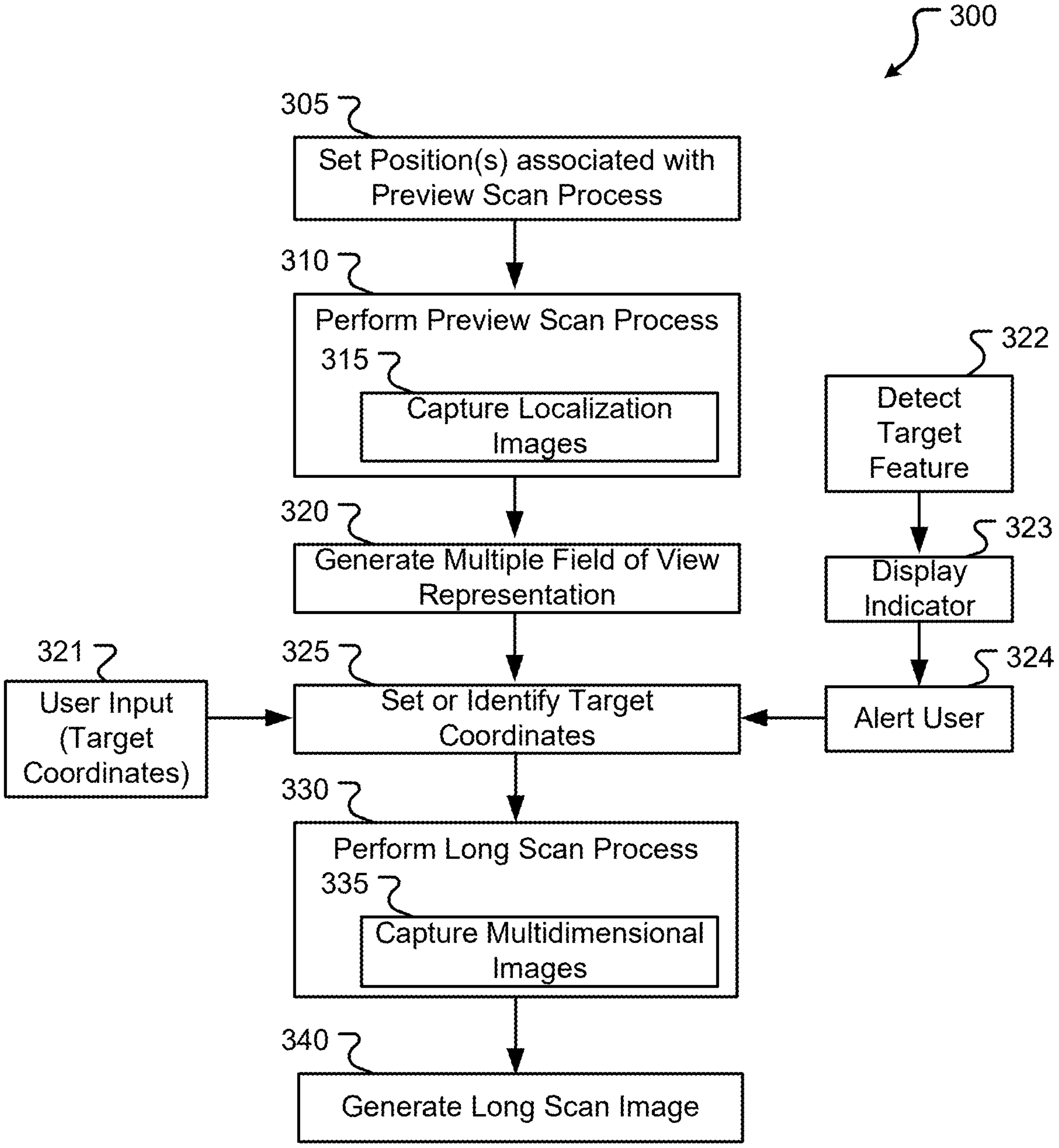
FIG. 3 illustrates an example of a process flow in accordance with aspects of the present disclosure.

FIG. 3 illustrates an example of a process flow 300 in accordance with aspects of the present disclosure. In some examples, process flow 300 may be implemented by aspects of the system 100 described herein.

In the following description of the process flow 300, the operations may be performed in a different order than the order shown, or the operations may be performed in different orders or at different times. Certain operations may also be left out of the process flow 300, or other operations may be added to the process flow 300.

It is to be understood that any device (e.g., computing device 102, imaging device 112, etc.) of the system 100 may perform the operations shown.

The process flow 300 is described herein with reference to FIG. 1C and FIGS. 2B through 2D.

At 305, the process flow 300 may include setting one or more positions associated with performing a preview scan process. The preview scan process may be associated with scanning a patient anatomy 210 associated with patient 148. In an example, setting the one or more positions may include setting a start position (e.g., position 160-*a*), one or more intermediate positions (e.g., position 160-*b*), and a stop position (e.g., position 160-*c*) associated with performing the preview scan process. In the example, the one or more intermediate positions (e.g., position 160-*b*, etc.) may be between the start position (e.g., position 160-*a*) and the stop position (e.g., position 160-*c*) with respect to an axis (e.g., X-axis).

In the example described herein, the patient anatomy 210 may include a spinal structure of the patient 148, but aspects of the present disclosure are not limited thereto. For example, the imaging techniques described herein may be implemented in association with generating long scans of other anatomical elements (e.g., soft tissue, tumors, other bone structures, etc.) of patient 148.

At 310, the process flow 300 may include performing the preview scan process.

At 315, in association with performing the preview scan process, the process flow 300 may include capturing localization images 205 of the patient anatomy 210, in which the localization images 205 are captured respective to the start position (e.g., position 160-*a*), the one or more intermediate positions (e.g., position 160-*b*), and the stop position (e.g., position 160-*c*).

For example, the system 100 may capture a localization image 205-*a* respective to position 160-*a*, capture a localization image 205-*b* (also referred to herein as an intermediate localization image) respective to position 160-*b*, and capture a localization image 205-*c* respective to position 160-*c*.

The localization images 205 may be scout images as described herein. For example, the system 100 may utilize the localization images 205 to define the scan range of a subsequent scan (e.g., an X-ray scan, a CT scan, an MRI scan, etc.) implemented in association with a long scan process. Examples of the long scan process are later described with reference to 330.

Figures 2C, 2D, 2E:
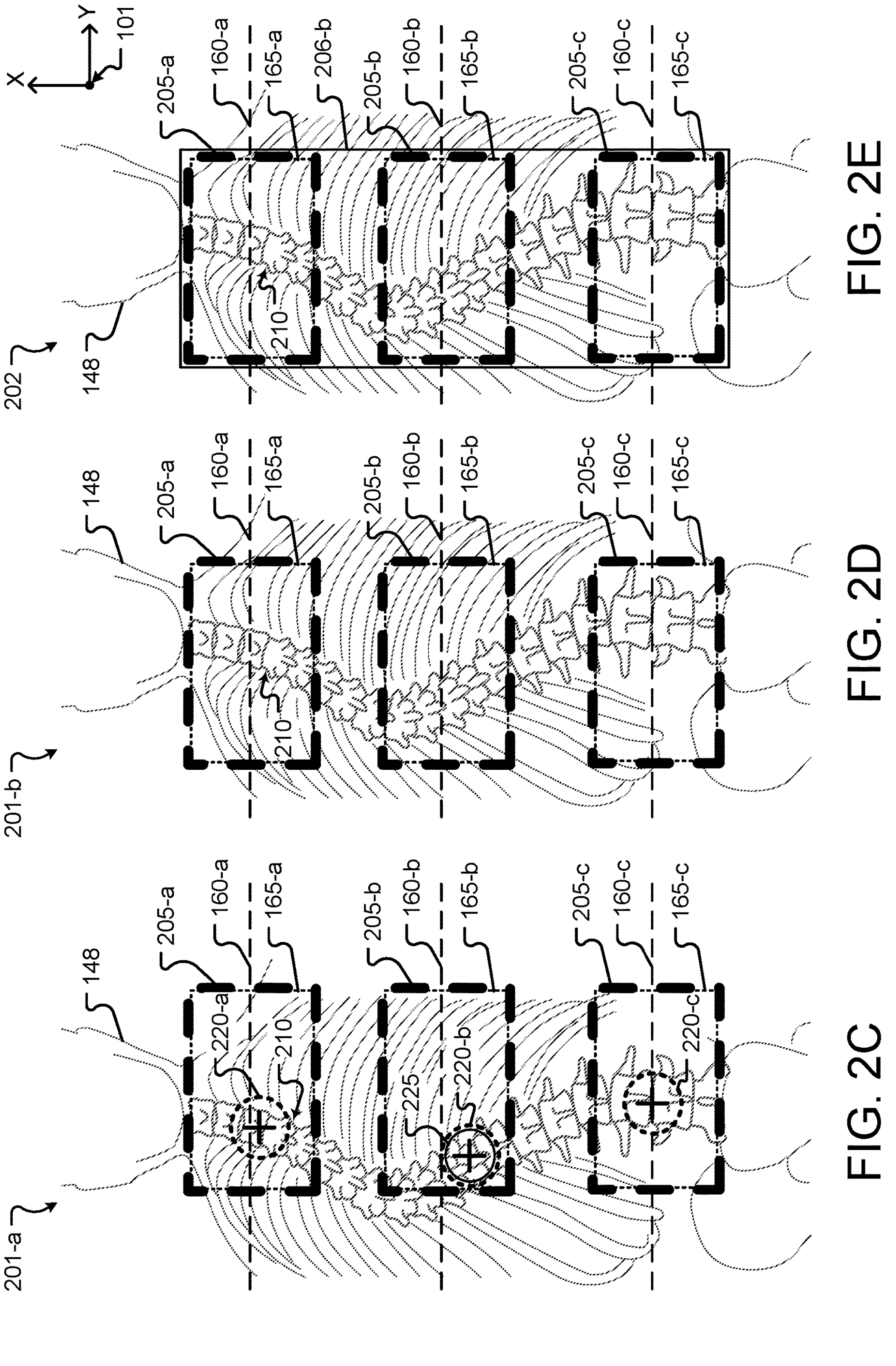

In an example, the localization image 205-*a* through localization image 205-*c* may each include a respective portion of the patient anatomy 210. The localization images 205 may include image data that respectively corresponds to regions 165 (as illustrated in FIG. 1C) and corresponding portions of the patient anatomy 210 (as illustrated in FIGS. 2B through 2D).

The localization images 205 may be overlapping or non-overlapping. For example, a localization image 205 (e.g., localization image 205-*b*, etc.) may at least partially overlap one or more other localization images 205 (e.g., localization image 205-*a*, localization image 205-*c*, etc.). Although not illustrated, in an example in which two localization images 205 overlap, a portion of the patient anatomy 210 may be captured in both localization images 205.

The localization images 205 may be equal or different in size. For example, a localization image 205 (e.g., localization image 205-*b*, etc.) may be equal in size or different in size compared to another localization image 205 (e.g., localization image 205-*a*, localization image 205-*c*, etc.).

It is to be understood that although a single intermediate localization image (e.g., localization image 205-*b*) is illustrated in FIGS. 2C through 2F, aspects of the present disclosure are not limited thereto. The systems and techniques described herein support capturing any quantity of intermediate localization images corresponding to respective positions located between the start position (e.g., position 160-*a*) and the stop position (e.g., position 160-*c*) with respect to an axis (e.g., X-axis).

Each of the localization images 205 may be an X-ray image, a CT image, an MRI image, an optical image, or a LiDAR image. In some aspects, the localization images 205 may include any combination of image types. In some example implementations, the localization images 205 may be of the same image type.

In some other example implementations, two or more of the localization images 205 may be of different image types. For example, the localization image 205-*a* may be a first image type (e.g., X-ray image), and the localization image 205-*b* and/or localization image 205-*c* may be a second image type (e.g., CT image, MRI image, optical image, LiDAR image, etc.). In the example of localization images 205 of different image types, the systems and techniques described herein may support merging image data of the first imaging type (e.g., X-ray imaging data) with image data of the second imaging type (e.g., CT imaging data, MRI imaging data, etc.).

Aspects of the present disclosure support setting any quantity of intermediate positions between the start position (e.g., position 160-*a*) and the stop position (e.g., position 160-*c*), and further, capturing intermediate localization images respective to the intermediate positions. It is to be understood that any of the aspects described herein association with respect to a singular intermediate localization image (e.g., localization image 205-*b*) may support implementations based on multiple intermediate localization images.

Figure 2F:
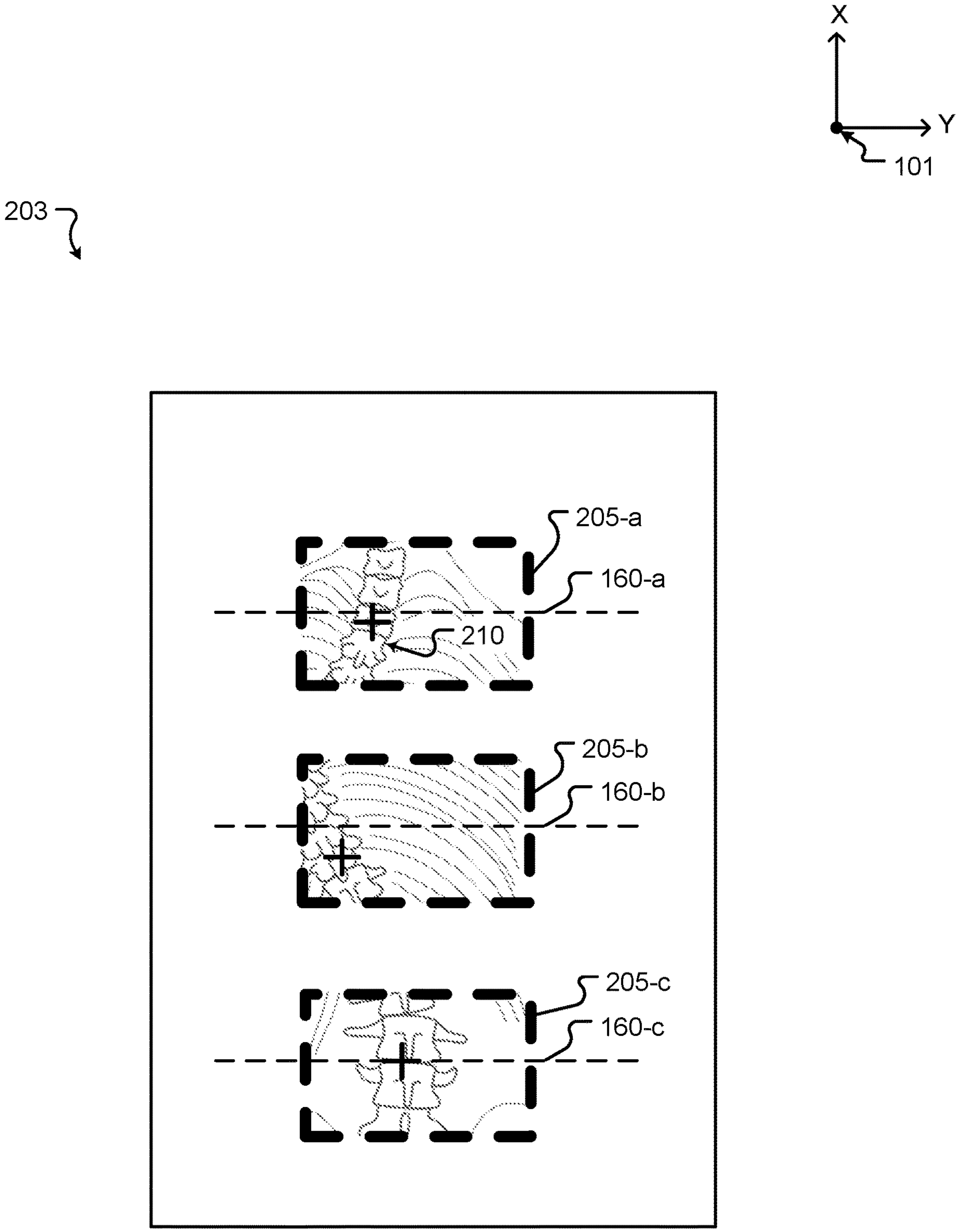

At 320, the process flow 300 may include generating a multiple field of view representation (e.g., multiple field of view representation 201-*a* illustrated in FIG. 2C, multiple field of view representation 201-*b* illustrated in FIG. 2D, multiple field of view representation 203 illustrated in FIG. 2F, etc.) of the patient anatomy 210 in response to performing the preview scan process.

The multiple field of view representation may display a full scan of a patient anatomy 210 in combination with indicators (e.g., dashed lines) corresponding to boundaries of the localization images 205, as illustrated in FIGS. 2C and 2D. In some other examples, the multiple field of view representation may display only the image data of the localization images 205, as illustrated in FIG. 2F. It is to be understood that any of the aspects described herein with reference to the process flow 300 may be applied to any of the multiple field of view representations (e.g., multiple field of view representation 201-*a*, multiple field of view representation 201-*b*, multiple field of view representation 203).

The system 100 may provide synchronized navigation of the localization image 205-*a*, the localization image 205-*b*, and the localization image 205-*c*. In an example, based on movement of the imaging device 112 (or other components of the system 100 associated with generating, viewing, and/or displaying the localization images 205), the system 100 may display the localization images 205 such that the movement is simultaneously reflected at all of the localization images 205. In an example, in response to movement of the imaging device 112 (or other components of the system 100 as described herein), the image data within the boundary boxes (represented by dotted lines in FIGS. 2C through 2F) of the localization images 205 may move together in synchronization.

At 325, the process flow 300 may include setting or identifying target coordinates (represented by a '+' at FIGS. 2C and 2F) associated with any or all of the localization images 205.

In an example, the system 100 may set or identify the target coordinates in response to a user input (at 321) associated with a localization image 205. For example, the user input may be a user selection (e.g., via a touchscreen displaying the localization image 205, using a mouse or controller input, etc.) of the target coordinates.

In another example, with reference to a localization image 205 (e.g., localization image 205-*b*), the user input may include a user selection of the target region 220 (also referred to herein as a region of interest) included in the localization image 205, and the target coordinates may correspond to the target region 220, be located inside of the target region 220, or the like. Examples of the target region 220 are illustrated at FIG. 2C.

In some other examples, the user input may include a user selection of a target feature 225 (also referred to herein as an object of interest) of the patient anatomy 210. In response to the user selection of the target feature 225, the system 100 may set target region 220-*b* corresponding to the target feature 225. In the example illustrated at FIG. 2C, the target region 220 may completely surround the target feature 225. Aspects of the present disclosure are not limited thereto, and the target feature 225 and the target region 220 may be different in size or equal in size.

In an example, referring to the example illustrated at FIG. 2D, the system 100 may recapture the localization images 205-*a* through 205-*c* based on the target coordinates and display updates to the localization images 205-*a* through 205-*c*. For example, the system 100 may shift the capture coordinates of the localization images 205-*a* through 205-*c* with respect to one or more axes (e.g., with respect to the Y-axis) based on the target coordinates. For example, FIG. 2D illustrates an example outcome of setting or adjusting the target coordinates in association with capturing patient anatomy (e.g., curvature 211 of the patient anatomy 210) that may potentially fail to be captured in a long scan process. In some aspects, the system 100 may support user confirmation of the updates and/or further user input (e.g., reselection of target coordinates, etc.).

The system 100 may perform a long scan process using the target coordinates, example aspects of which are later described herein with reference to 330 of the process flow 300. For example, the system 100 may capture multidimensional images based on the localization images 205 and the respective target coordinates for each localization image 205 as described with reference to FIG. 2C, such that each multidimensional image is centered with respect to the respective target coordinates. In some aspects, based on the target coordinates, the system 100 may set or calculate an image acquisition path for performing the long scan process.

Accordingly, for example, via a multiple field of view representation as described herein, the systems and techniques may support user selection of desired centers of localization images 205. Accordingly, for example, by setting the desired centers of localization images 205, the user may set desired centers of corresponding multidimensional images to be captured in the long scan process.

The system 100 may support AI and computer vision based selection of the target coordinates for any or all of the localization images 205. For example, with reference to the example at FIG. 2C, at 322 of the process flow 300, the system 100 may detect a target feature 225 (e.g., using object detection 129 described with reference to FIG. 1A). At 323, the system 100 may display an indicator (e.g., highlighting, outline, etc.) corresponding to the target feature 225 and/or an indicator (e.g., a circle, a dotted circle, a rectangle, etc.) corresponding to a target region 220-*b*. In some aspects, returning to 325, the system 100 may set candidate target coordinates (e.g., represented by indicator '+') in association with the target feature 225.

In some examples, at 324, the system 100 may alert the user of a candidate object of interest (e.g., the target feature 225) included in the localization image 205-*b* and the candidate target coordinates. In some aspects, the system 100 may support features for user confirmation (e.g., approval, denial) and user modification of the candidate target coordinates. In some example implementations the system 100 may identify and/or set the target coordinates without a user input.

At 330, the process flow 300 may include performing a long scan process associated with scanning the patient 148 based on the localization image 205-*a*, the localization image 205-*b* (or multiple intermediate localization images), and the localization image 205-*c*. In an example of performing the long scan process, the system 100 may capture multidimensional images (e.g., 2D or 3D) including the patient anatomy 210 based on the localization image 205-*a*, the localization image 205-*b*, and the localization image 205-*c*. In an example, the multidimensional images may be X-ray images, CT images, or MRI images, but are not limited thereto.

In an example of performing the long scan process, at 335, the system 100 may capture multidimensional images based on the target coordinates associated with the localization images 205. For example, the system 100 may capture the multidimensional images such that the multidimensional images are centered with respect to the respective target coordinates described with reference to 325. In an example, the system 100 may capture a multidimensional image corresponding to a localization image 205 (e.g., localization image 205-*a*, localization image 205-*b*, etc.) such that the multidimensional image is centered with respect to the respective target coordinates ('+') as set by a user and/or the system 100.

At 340, the system 100 may generate a long scan image 206-*b* including the patient anatomy 210 as described herein. For example, the system 100 may generate the long scan image 206-*b* based on the multidimensional images captured at 335. In an example, the system 100 may merge the data from the multidimensional images into the long scan image 206-*b* (e.g., capture and "stitch" together the multidimensional images).

Accordingly, as described with reference to the process flow 300, the systems and techniques described herein support operator based adjustment to localization images 205 (e.g., user selection or confirmation of target coordinates, target regions 220, target features 225, etc.), and the system 100 may capture and stich together multidimensional images which correspond to the localization images 205.

Aspects of the present disclosure may be implemented based on localization images 205 of any image type. For example, the localization images 205 may include localization images captured from any angle (e.g., any angle with respect to the patient 148) or any plane of orientation. Non-limiting examples of the image types include posterior-anterior images, anterior-posterior images, lateral images, oblique images, axial images, coronal images, sagittal images, and the like.

Aspects of the present disclosure support setting target coordinates (and shifting capture coordinates based on the target coordinates) with respect to any axis of the coordinate system 101. For example, the localization images 205 may be posterior-anterior images, and the system 100 may support setting target coordinates (and shifting capture coordinates based on the target coordinates) with respect to the X-axis and Y-axis of the coordinate system 101. In another example, the localization images 205 may be lateral images of the patient 148, and the system 100 may support setting target coordinates (and shifting capture coordinates based on the target coordinates) with respect to the X-axis and Z-axis of the coordinate system 101.

Accordingly, for example, as described with reference to the process flow 300, the systems and techniques described herein support generating a long scan image 206-*b* which captures a portion (e.g., a curvature 211) of the patient anatomy 210 that might otherwise fail to be captured.

The systems and techniques described herein support setting parameters associated with the long scan process. In an example aspect, in capturing the multidimensional images, the system 100 may adjust one or more parameters associated with the imaging device 112 such that radiation emitted from the source 138 is focused on the target coordinates associated with each localization image 205.

In another example aspect, the system 100 may support setting parameters of an image acquisition path associated with the long scan process, and the image acquisition path may be a fixed path or modifiable. For example, the system 100 may calculate one or more parameters associated with an image acquisition path based on the localization image 205-*a*, the localization image 205-*b*, and the localization image 205-*c*, and the system 100 may perform the long scan process based on the one or more parameters and the image acquisition path.

In an example implementation in which the imaging device 112 is an O-arm, the image acquisition path associated with capturing the localization images 205 and the multidimensional images may be a linear path, for example, due to features of the O-arm associated with capturing images. The system 100 may identify image capture coordinates along the linear path for capturing the multidimensional images. That is, for example, though the initial image capture coordinates associated with the localization images 205 may correspond to position 160-*a* through position 160-*c*, the system 100 may set the image capture coordinates for capturing the multidimensional images, in which the image capture coordinates correspond to (e.g., with reference to the X-axis and/or Y-axis) the target coordinates ('+') associated with the localization images 205. The image capture coordinates may be different from respective centers of the localization images 205.

It is to be understood that aspects of the present disclosure described herein may be applied to image capture paths other than linear paths. For example, in some alternative and/or additional implementations, the system 100 may set an image acquisition path for capturing images with respect to three dimensions, and the image acquisition path may include image capture coordinates and/or device movement with respect to any of the X, Y, and Z axes.

Figure 4:
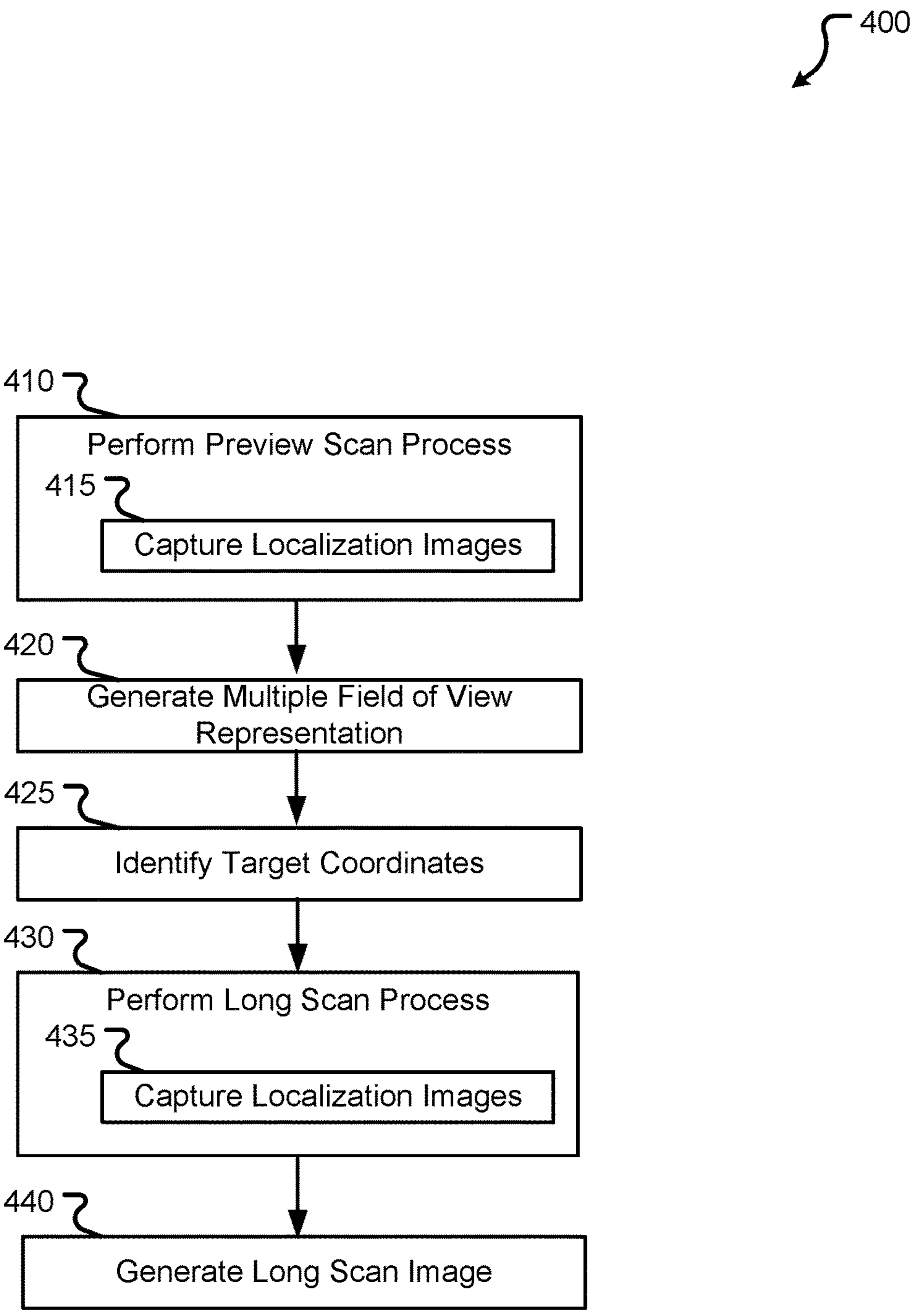
FIG. 4 illustrates an example of a process flow in accordance with aspects of the present disclosure.

FIG. 4 illustrates an example of a process flow 400 in accordance with aspects of the present disclosure.

In some examples, process flow 400 may be implemented by aspects of the system 100 described herein.

In the following description of the process flow 400, the operations may be performed in a different order than the order shown, or the operations may be performed in different orders or at different times. Certain operations may also be left out of the process flow 400, or other operations may be added to the process flow 400.

It is to be understood that any device (e.g., computing device 102, imaging device 112, etc.) of the system 100 may perform the operations shown.

At 410, the process flow 400 may include performing a preview scan process associated with scanning a patient anatomy.

In some aspects, performing the preview scan process includes (at 415): capturing a first localization image based on a start position associated with the preview scan process; capturing a second localization image based on a stop position associated with the preview scan process; and capturing one or more intermediate localization images based on one or more intermediate positions different from the start position and the stop position.

In some aspects, the one or more intermediate positions are between the start position and the stop position with respect to a first axis.

In some aspects, the first localization image includes at least a first portion of the patient anatomy, the second localization image includes at least a second portion of the patient anatomy, and the one or more intermediate localization images include at least a third portion of the patient anatomy.

In some examples, the first localization image, the second localization image, and the one or more intermediate localization images each include an X-ray image, a CT image, an MRI image, an optical image, or a LiDAR image.

At 420, the process flow 400 may include generating a multiple field of view representation of the patient anatomy in response to performing the preview scan process. In some aspects, generating the multiple field of view representation includes providing synchronized navigation of the first localization image, the second localization image, and the one or more intermediate localization images.

At 425, the process flow 400 may include identifying target coordinates corresponding to a target region included in at least one localization image among the first localization image, the second localization image, and the one or more intermediate localization images, wherein performing the long scan process is based on the target coordinates.

In some aspects, identifying the target coordinates is in response to a user selection of at least one of: the target region included in the at least one localization image; and a target portion of the patient anatomy, wherein the target portion is included in the target region.

In some aspects, identifying the target coordinates is in response to detecting a target feature included in the target region, wherein the target feature is associated with the patient anatomy.

In some aspects, the target region included in the at least one localization image includes at least a portion of the patient anatomy.

At 430, the process flow 400 may include performing a long scan process associated with scanning the patient anatomy based on the first localization image, the second localization image, and the one or more intermediate localization images.

In some aspects, performing the long scan process may include (at 435): capturing a set of multidimensional images including the patient anatomy based on the first localization image, the second localization image, and the one or more intermediate localization images.

In some aspects, the set of multidimensional images may include an X-ray image, a CT image, or an MRI image.

At 440, the process flow 400 may include generating a long scan image including the patient anatomy based on merging data associated with the set of multidimensional images.

In some examples, the patient anatomy includes a spinal structure. In an example, the long scan image depicts at least a curved portion of the patient anatomy. In some other examples, the patient anatomy includes soft tissue (e.g., tumors, etc.).

In some example implementations, the process flow 400 may include calculating one or more parameters associated with an image acquisition path based on the first localization image, the second localization image, and the one or more intermediate localization images.

In some aspects, the process flow 400 may include calculating the one or more parameters associated with the image acquisition path based on the target coordinates. In an example, the process flow 400 may include performing the long scan process (at 430) associated with scanning the patient anatomy based on the one or more parameters associated with the image acquisition path.

The process flow 400 (and/or one or more operations thereof) may be carried out or otherwise performed, for example, by at least one processor. The at least one processor may be the same as or similar to the processor(s) 104 of the computing device 102 described above. The at least one processor may be part of an imaging system (including the imaging device 112), a robot (such as a robot 114) or part of a navigation system (such as a navigation system 118). A processor other than any processor described herein may also be used to execute the process flow 400. The at least one processor may perform operations of the process flow 400 by executing elements stored in a memory such as the memory 106. The elements stored in memory and executed by the processor may cause the processor to execute one or more operations of a function as shown in the process flow 400. One or more portions of the process flow 400 may be performed by the processor executing any of the contents of memory, such as image processing 120, a segmentation 122, a transformation 124, a registration 128, and/or object detection 129.

As noted above, the present disclosure encompasses methods with fewer than all of the features identified in FIGS. 3 and 4 (and the corresponding description of the process flows 300 and 400), as well as methods that include additional features beyond those identified in FIGS. 3 and 4 (and the corresponding description of the process flows 300 and 400). The present disclosure also encompasses methods that include one or more steps from one method described herein, and one or more steps from another method described herein. Any correlation described herein may be or include a registration or any other correlation.

The foregoing is not intended to limit the disclosure to the form or forms disclosed herein. In the foregoing Detailed Description, for example, various features of the disclosure are grouped together in one or more aspects, implementations, and/or configurations for the purpose of streamlining the disclosure. The features of the aspects, implementations, and/or configurations of the disclosure may be combined in alternate aspects, implementations, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, implementation, and/or configuration. Thus, the following claims are hereby incorporated into this Detailed Description, with each claim standing on its own as a separate preferred implementation of the disclosure.

Moreover, though the foregoing has included description of one or more aspects, implementations, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, implementations, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

Example aspects of the present disclosure include:

A system including: a processor; and a memory storing instructions thereon that, when executed by the processor, cause the processor to: perform a preview scan process associated with scanning a patient anatomy, wherein performing the preview scan process includes: capturing a first localization image based on a start position associated with the preview scan process; capturing a second localization image based on a stop position associated with the preview scan process; and capturing one or more intermediate localization images based on one or more intermediate positions different from the start position and the stop position; and perform a long scan process associated with scanning the patient anatomy based on the first localization image, the second localization image, and the one or more intermediate localization images.

Any of the aspects herein, wherein the instructions are further executable by the processor to: calculate one or more parameters associated with an image acquisition path based on the first localization image, the second localization image, and the one or more intermediate localization images; and perform the long scan process associated with scanning the patient anatomy based on the one or more parameters associated with the image acquisition path.

Any of the aspects herein, wherein the instructions are further executable by the processor to: generate a multiple field of view representation of the patient anatomy in response to performing the preview scan process, wherein generating the multiple field of view representation includes providing synchronized navigation of the first localization image, the second localization image, and the one or more intermediate localization images.

Any of the aspects herein, wherein: the first localization image includes at least a first portion of the patient anatomy; the second localization image includes at least a second portion of the patient anatomy; and the one or more intermediate localization images include at least a third portion of the patient anatomy.

Any of the aspects herein, wherein the one or more intermediate positions are between the start position and the stop position with respect to a first axis.

Any of the aspects herein, wherein the instructions are further executable by the processor to: identify target coordinates corresponding to a target region included in at least one localization image among the first localization image, the second localization image, and the one or more intermediate localization images, wherein performing the long scan process is based on the target coordinates.

Any of the aspects herein, wherein the instructions are further executable by the processor to: calculate one or more parameters associated with an image acquisition path based on the target coordinates; and perform the long scan process associated with scanning the patient anatomy based on the one or more parameters associated with the image acquisition path.

Any of the aspects herein, wherein identifying the target coordinates is in response to a user selection of at least one of: the target region included in the at least one localization image; and a target portion of the patient anatomy, wherein the target portion is included in the target region.

Any of the aspects herein, wherein identifying the target coordinates is in response to detecting a target feature included in the target region, wherein the target feature is associated with the patient anatomy.

Any of the aspects herein, wherein: the target region included in the at least one localization image includes at least a portion of the patient anatomy.

Any of the aspects herein, wherein the instructions executable by the processor to perform the long scan process are further executable by the processor to: capture a set of multidimensional images including the patient anatomy based on the first localization image, the second localization image, and the one or more intermediate localization images; and generate a long scan image including the patient anatomy based on merging data associated with the set of multidimensional images.

Any of the aspects herein, wherein the set of multidimensional images include an X-ray image, a computed tomography (CT) image, or a magnetic resonance imaging (MRI) image.

Any of the aspects herein, wherein the long scan image depicts at least a curved portion of the patient anatomy.

Any of the aspects herein, wherein the patient anatomy includes a spinal structure.

Any of the aspects herein, wherein the patient anatomy includes soft tissue.

Any of the aspects herein, wherein: the first localization image, the second localization image, and the one or more intermediate localization images each include an X-ray image, a computed tomography (CT) image, a magnetic resonance imaging (MRI) image, an optical image, or a light detection and ranging (LiDAR) image.

An imaging device; a processor coupled with the imaging device; and memory coupled with the processor and storing instructions thereon that, when executed by the processor, enable the processor to: perform a preview scan process associated with scanning a patient anatomy, wherein performing the preview scan process includes: capturing a first localization image based on a start position associated with the preview scan process; capturing a second localization image based on a stop position associated with the preview scan process; and capturing one or more intermediate localization images based on one or more intermediate positions different from the start position and the stop position; and perform a long scan process associated with scanning the patient anatomy using the imaging device, wherein performing the long scan process is based on the first localization image, the second localization image, and the one or more intermediate localization images.

Any of the aspects herein, wherein the instructions are further executable by the processor to: generate a multiple field of view representation of the patient anatomy in response to performing the preview scan process, wherein generating the multiple field of view representation includes providing synchronized navigation of the first localization image, the second localization image, and the one or more intermediate localization images.

Any of the aspects herein, wherein the imaging device includes at least one of an O-arm and a C-arm.

A method including: performing a preview scan process associated with scanning a patient anatomy, wherein performing the preview scan process includes: capturing a first localization image based on a start position associated with the preview scan process; capturing a second localization image based on a stop position associated with the preview scan process; and capturing one or more intermediate localization images based on one or more intermediate positions different form the start position and the stop position; and performing a long scan process associated with scanning the patient anatomy based on the first localization image, the second localization image, and the one or more intermediate localization images.

Any of the aspects herein, further including: generating a multiple field of view representation of the patient anatomy in response to performing the preview scan process, wherein generating the multiple field of view representation includes providing synchronized navigation of the first localization image, the second localization image, and the one or more intermediate localization images.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/implementations in combination with any one or more other aspects/features/implementations.

Use of any one or more of the aspects or features as disclosed herein.

It is to be appreciated that any feature described herein can be claimed in combination with any other feature(s) as described herein, regardless of whether the features come from the same described implementation.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an implementation that is entirely hardware, an implementation that is entirely software (including firmware, resident software, micro-code, etc.) or an implementation combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

What is claimed is:

1. A system comprising:

a processor; and a memory storing instructions thereon that, when executed by the processor, cause the processor to:

perform a preview scan process associated with scanning a patient anatomy including a first portion, a second portion different from the first portion, and a third portion different from the first portion and the second portion;

perform a long scan process associated with scanning the patient anatomy based on the preview scan process, wherein performing the preview scan process comprises:

capturing a first localization image of the first portion of the patient anatomy based on a start position associated with the long scan process, wherein the first localization image includes the start position;

capturing a second localization image of the second portion of the patient anatomy based on a stop position associated with the long scan process, wherein the second localization image includes the stop position; and capturing at least one third localization image including one or more intermediate localization images of the third portion of the patient anatomy based on one or more intermediate positions different from the start position and the stop position and positioned between the start position and the stop position with respect to a first axis associated with acquisition of a long scan image from the long scan process, wherein the at least one third localization image includes the one or more intermediate positions;

generate, in response to performing the preview scan process, a multiple field of view representation of the patient anatomy based on the first localization image, the second localization image, and the at least one third localization image; and identify, from the multiple field of view representation, target coordinates associated with each of the first localization image, the second localization image, and the at least one third localization image, wherein performing the long scan process comprises:

performing the long scan process using the target coordinates from the start position to the stop position and including the one or more intermediate positions along an image acquisition path passing through at least a portion of the first localization image, the second localization image, and the at least one third localization image, and in accordance with one or more parameters associated with the image acquisition path, wherein the one or more parameters are set based on the first localization image, the second localization image, and the at least one third localization image;

capturing a plurality of multidimensional images during the long scan process along the image acquisition path; and generating the long scan image based on the plurality of multidimensional images.

2. The system of claim 1, wherein the instructions are further executable by the processor to:

calculate the one or more parameters associated with the image acquisition path based on the first localization image, the second localization image, and the one or more intermediate localization images.

3. The system of claim 1, wherein, when executed to generate the multiple field of view representation, the instructions cause the processor to provide synchronized navigation of the first localization image, the second localization image, and the one or more intermediate localization images.

4. The system of claim 3, wherein the instructions are further executable by the processor to adjust one or more parameters associated with an imaging device utilized for the long scan process for capturing the plurality of multidimensional images to cause radiation emitted from a source of the imaging device to be focused on the target coordinates associated with each of the first localization image, the second localization image, and the at least one third localization image.

5. The system of claim 1, wherein the instructions are further executable by the processor to acquire, based on the long scan process, the long scan image having a size that is greater than a corresponding size of each of the first localization image, the second localization image, and the one or more intermediate localization images at least with respect to a dimension corresponding to a scan direction along the first axis associated with acquisition of the long scan image.

6. The system of claim 1, wherein the target coordinates correspond to a target region comprised in at least one localization image among the first localization image, the second localization image, and the one or more intermediate localization images.

7. The system of claim 6, wherein the instructions are further executable by the processor to adjust one or more parameters associated with an imaging device utilized for the long scan process for capturing the plurality of multidimensional images to cause radiation emitted from a source of the imaging device to be focused on the target coordinates associated with each of the first localization image, the second localization image, and the at least one third localization image.

8. The system of claim 6, wherein, when executed to identify the target coordinates, the instructions cause the processor to identify the target coordinates corresponding to the target region in response to a user selection of at least one of:

the target region comprised in the at least one localization image; and a target portion of the patient anatomy, wherein the target portion is comprised in the target region.

9. The system of claim 6, wherein, when executed to identify the target coordinates, the instructions cause the processor to identifying the target coordinates corresponding to the target region in response to detecting a target feature comprised in the target region, wherein the target feature is associated with the patient anatomy.

10. The system of claim 6, wherein the target region is comprised in the at least one localization image comprising at least a portion of the patient anatomy.

11. The system of claim 1, wherein, when executed to perform the long scan process, the instructions cause the processor to generate a long scan image comprising the patient anatomy based on merging data associated with the plurality of multidimensional images.

12. The system of claim 11, wherein the plurality of multidimensional images comprise an X-ray image, a computed tomography (CT) image, or a magnetic resonance imaging (MRI) image.

13. The system of claim 11, wherein at least one of:

the long scan image depicts at least a curved portion of the patient anatomy; and the patient anatomy comprises a spinal structure or soft tissue.

14. The system of claim 1, wherein, when executed to capture the plurality of multidimensional images, the instructions cause the processor to capture each multidimensional image of the plurality of multidimensional images centered with respect to its corresponding target coordinates.

15. The system of claim 1, wherein the first portion, the second portion, and the third portion of the patient anatomy are non-overlapping.

16. The system of claim 1, wherein the first localization image, the second localization image, and the one or more intermediate localization images each comprise an X-ray image, a computed tomography (CT) image, a magnetic resonance imaging (MRI) image, an optical image, or a light detection and ranging (LiDAR) image.

17. A system comprising:

an imaging device;

a processor coupled with the imaging device; and memory coupled with the processor and storing instructions thereon that, when executed by the processor, enable the processor to:

perform a preview scan process associated with scanning a patient anatomy including a first portion, a second portion different from the first portion, and a third portion different from the first portion and the second portion;

perform a long scan process associated with scanning the patient anatomy based on the preview scan process, wherein performing the preview scan process comprises:

capturing a first localization image of the first portion of the patient anatomy based on a start position associated with the long scan process, wherein the first localization image includes the start position;

capturing a second localization image of the second portion of the patient anatomy based on a stop position associated with the long scan process, wherein the second localization image includes the stop position; and capturing at least one third localization image including one or more intermediate localization images of the third portion of the patient anatomy based on one or more intermediate positions different from the start position and the stop position and positioned between the start position and the stop position with respect to a first axis associated with acquisition of a long scan image from the long scan process, wherein the at least one third localization image includes the one or more intermediate positions; and generate, in response to performing the preview scan process, a multiple field of view representation of the patient anatomy based on the first localization image, the second localization image, and the at least one third localization image; and identify, from the multiple field of view representation, target coordinates associated with each of the first localization image, the second localization image, and the at least one third localization image, wherein performing the long scan process comprises:

performing the long scan process using the target coordinates from the start position to the stop position and including the one or more intermediate positions along an image acquisition path passing through at least a portion of the first localization image, the second localization image, and the at least one third localization image, and in accordance with one or more parameters associated with the image acquisition path, wherein the one or more parameters are set based on the first localization image, the second localization image, and the at least one third localization image;

capturing a plurality of multidimensional images during the long scan process along the image acquisition path; and generating the long scan image based on the plurality of multidimensional images.

18. The system of claim 17, wherein generating the multiple field of view representation comprises providing synchronized navigation of the first localization image, the second localization image, and the one or more intermediate localization images.

19. A method comprising:

performing a preview scan process associated with scanning a patient anatomy including a first portion, a second portion different from the first portion, and a third portion different from the first portion and the second portion; and performing a long scan process associated with scanning the patient anatomy based on the preview scan process, wherein performing the preview scan process comprises:

capturing a first localization image of the first portion of the patient anatomy based on a start position associated with the long scan process, wherein the first localization image includes the start position;

capturing a second localization image of the second portion of the patient anatomy based on a stop position associated with the long scan process, wherein the second localization image includes the stop position; and capturing at least one third localization image including one or more intermediate localization images of the third portion of the patient anatomy based on one or more intermediate positions different from the start position and the stop position and positioned between the start position and the stop position with respect to a first axis associated with acquisition of a long scan image from the long scan process, wherein the at least one third localization image includes the one or more intermediate positions;

in response to performing the preview scan process, generating a multiple field of view representation of the patient anatomy based on the first localization image, the second localization image, and the at least one third localization image; and identifying, from the multiple field of view representation, target coordinates associated with each of the first localization image, the second localization image, and the at least one third localization image, wherein performing the long scan process comprises:

performing the long scan process using the target coordinates from the start position to the stop position and including the one or more intermediate positions along an image acquisition path passing through at least a portion of the first localization image, the second localization image, and the at least one third localization image, and in accordance with one or more parameters associated with the image acquisition path, wherein the one or more parameters are set based on the first localization image, the second localization image, and the at least one third localization image;

capturing a plurality of multidimensional images during the long scan process along the image acquisition path; and generating the long scan image based on the plurality of multidimensional images.

20. The method of claim 19, wherein generating the multiple field of view representation comprises providing synchronized navigation of the first localization image, the second localization image, and the one or more intermediate localization images.

* * * * *